United States Patent [19]

Ott

[11] Patent Number: 4,849,423

[45] Date of Patent: Jul. 18, 1989

[54] PURINE DERIVATIVES, MEDICAMENTS CONTAINING THEM AND METHODS OF TREATING CARDIAC INSUFFICIENCIES AND IRREGULARITIES WITH THEM.

[75] Inventor: Hans Ott, Pfeffingen, Switzerland

[73] Assignee: Sandoz Ltd., Basel, Switzerland

[21] Appl. No.: 13,516

[22] Filed: Feb. 11, 1987

[30] Foreign Application Priority Data

Feb. 14, 1986 [DE] Fed. Rep. of Germany ....... 3604743
Apr. 17, 1986 [DE] Fed. Rep. of Germany ....... 3612953

[51] Int. Cl.$^4$ .................... A61K 31/52; C07D 473/02; C07D 473/26; C07D 473/32

[52] U.S. Cl. .................................... 514/253; 514/261; 514/262; 514/266; 544/264; 544/265; 544/271; 544/272; 544/276; 544/277

[58] Field of Search ............... 544/277, 276, 264, 265, 544/272, 271; 514/261, 262, 266, 253

[56] References Cited

U.S. PATENT DOCUMENTS

| | | | |
|---|---|---|---|
| 3,457,263 | 7/1969 | Regnier et al. | 544/277 |
| 3,459,753 | 8/1969 | Boltze et al. | 544/270 |
| 3,642,798 | 2/1972 | Nitta et al. | 544/270 |
| 3,919,226 | 11/1975 | Thiel et al. | 544/277 |
| 4,426,383 | 1/1984 | Sugimoto et al. | 514/283 |
| 4,543,254 | 9/1985 | Kaneko et al. | 514/253 |

OTHER PUBLICATIONS

Ikeda et al., Chemical Abstracts, vol. 71: 61339e (1969).
Zejc, et al., Chemical Abstracts, vol. 86: 89761v (1977).
Zejc, et al. Chemical Abstracts, vol. 90: 103924s (1979).
Mirecka, et al., Chemical Abstracts, vol. 94: 229x (1981).

*Primary Examiner*—Donald G. Daus
*Assistant Examiner*—Diana G. Rivers
*Attorney, Agent, or Firm*—Gerald D. Sharkin; Robert S. Honor; Thomas O. McGovern

[57] ABSTRACT

The compounds of formula I, in free form or in salt form have cardiotonic and antiarrhythmic activity. They may be used as medicaments. They are obtained by means of appropriate 3-amino-2-hydroxy-propylation of purines.

11 Claims, No Drawings

PURINE DERIVATIVES, MEDICAMENTS CONTAINING THEM AND METHODS OF TREATING CARDIAC INSUFFICIENCIES AND IRREGULARITIES WITH THEM.

The invention relates to the compounds of formula I,

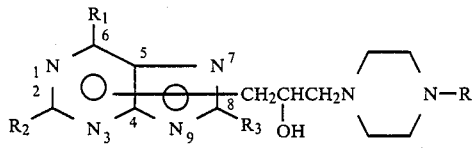

wherein

R signifies diphenylalkyl with 13 to 17 carbon atoms or diphenylalkyl with 13 to 17 carbon atoms which is monosubstituted or disubstituted by the same or different substituents in one or both phenyl rings by alkyl with 1 to 4 carbon atoms, alkoxy with 1 to 4 carbon atoms and/or halogen with an atomic number of 9 to 35, $R_1$ denotes hydrogen, halogen with an atomic number of 9 to 35, amino, alkylamino with 1 to 4 carbon atoms, dialkylamino with independently 1 to 4 carbon atoms in the alkyl radicals, 1-pipe-ridino, alkanoylamino with a total of 2 to 5 carbon atoms, hydroxy, alkoxy with 1 to 4 carbon atoms, sulphhydryl, alkylthio with 1 to 4 carbon atoms, benzoylamino or pyridinylcarbonylamino, $R_2$ signifies hydrogen, hydroxy, amino or alkanoylamino with a total of 2 to 5 carbon atoms and $R_3$ signifies hydrogen, alkyl with 1 to 4 carbon atoms, trifluoromethyl, Amino or halogen with an atomic number of 9 to 35,
in free form or in salt form.

The compounds of formula I may exist in tautomeric form. Such tautomeric forms also fall within the scope of the present invention. The compounds of formula I are in the following also named compounds according to the invention.

As can be seen from formula I, the side chain is bonded to a nitrogen atom.

The side chain is preferably bonded in position 3, 7 or 9 of the purine frame, especially position 3 or 9.

The alkylene part of diphenylalkyl preferably contains 1, 3 or 4, especially 1 or 4 carbon atom(s). The phenyl rings of diphenylalkyl are preferably unsubstituted. If they are substituted, they are each preferably mono-substituted, especially in meta- or para-, especially in para-position. If they are di-substituted, they are preferably substituted in meta- and para-position. If they are substituted, they are preferably substituted by halogen or alkoxy, especially by halogen and the substituents are preferably identical.

Alkyl and/or alkoxy and/or alkylthio and/or the alkyl part of alkylamino or dialkylamino preferably contains 1 to 3, especially 1 carbon atom(s). Halogen preferably signifies fluorine or chlorine or bromine. The alkyl parts of dialkylamino are preferably identical.

R preferably signifies diphenylmethyl, preferably unsubstituted. $R_1$ preferably denotes hydrogen, halogen, amino, benzoylamino, acetylamino, piperidino, alkylamino, dialkylamino, hydroxy or alkoxy, especially amino, alkylamino, dialkylamino or alkoxy, especially amino. $R_2$ preferably denotes hydrogen. $R_3$ preferably denotes hydrogen, alkyl, trifluormethyl or halogen, especially chlorine or bromine, especially hydrogen.

The compounds according to the invention are obtained by appropriate 3-amino-2-hydroxy-propylation of corresponding compounds of formula II

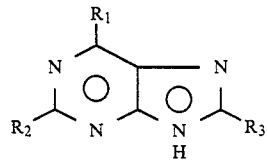

wherein $R_1$ to $R_3$ are defined as above. Especially compounds of formula II are reacted with corresponding compounds of formula III

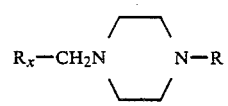

wherein R is defined as above and $R_x$ denotes a group which yields a 1-hydroxyethyl group reacting with a purine.

The process according to the invention may take place under conditions which are known for the production of analogous compounds, which are discussed in the following examples.

The choise of the most suitable variant should of course be made whilst taking into consideration the reactivities of the substituents available, if necessary giving temporary protection of any sensitive groups and subsequently splitting off or converting the protecting groups. Thus e.g. an amino group on the purine ring can be transformed by means of diazotisation and subsequent boiling down into the hydroxy group; an amino group is position 6 of the purine ring can e.g. also be transformed into an alkanoylamino, benzoylamino or pyridinylcarbonylamino group by reacting with an alkanoyl-, benzoyl- or pyridinecarbonylchloride.

Primary products of the compounds of formula II are compounds which can be reacted to form compounds of formula II, e.g. by means of appropriate splitting off protecting groups or by transformation.

The process according to the invention can therefore be effected in more than one operation.

The group $R_x$ employed is for example the group

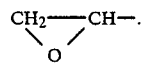

The reaction is performed preferably in the presence of a solvent. The solvent used is preferably methanol, ethanol or a suitable ether, e.g. dioxane. Suitable temperatures are about 20° to 150° C. It is convenient to operate at reflux temperature if a solvent is present. The process is preferably effected under alkaline conditions e.g. in presence of caustic soda.

The compounds according to the invention can be isolated from the reaction mixture and purified by known methods, e.g. by chromatography.

The compounds according to the invention may exist in free form, i.e. normally as a base, or in salt form. Salts, e.g. acid addition salts, e.g. with hydrochloric, malonic, maleinic or fumaric acid, may be obtained in known manner from the compounds in free form, and vice versa.

In the compounds according to the invention, the propanol side chain is chiral; they may therefore appear in racemic form or in the form of the corresponding enantiomers. Should a further centre of chirality exist, the compounds may appear in the form of stereoisomer mixtures or the corresponding pure enantiomers. Should they appear in optically active form, preference is given to those optically active forms in which the S-configuration is present on the asymmetrically substituted carbon atom of the side chain which bears the hydroxy group. The individual enantiomers or resp. diastereoisomeric mixtures of the compounds according to the invention may be obtained in known manner, e.g. by using the corresponding enantiomers or resp. racemates of the starting compounds, or by means of fractionated crystallisation of salts of individual, optionally diastereoisomeric racemates with optically active acids.

Insofar as the production of the required starting materials is not described, these are known or may be produced by known processes, or analogously to the processes described here or analogously to known processes.

In the following examples, all temperatures are given in degrees celsius and are uncorrected.

EXAMPLES 1 TO 3

6-amino-α-[(4-diphenylmethyl-1-piperazinyl)-methyl]-3H-purine-3-ethanol (Example 1), 6-amino-α-[(4-diphenylmethyl-1-piperazinyl)-methyl]-9H-purine-9-ethanol (Example 2) and 6-amino-α-[(4-diphenylmethyl-1-piperazinyl)-methyl]-7H-purine-7-ethanol (Example 3)

13.5 g of adenine and 30.8 g of 1-diphenylmethyl-4-(2,3-epoxy-propyl)-piperazine are refluxed for 1 hour in 100 ml of 1N caustic soda and 100 ml of dioxane. After cooling the reacting mixture, it is diluted with 100 ml of water and extracted several times with ethyl acetate. The combined organic phases are dried over sodium sulphate, filtered and evaporated under vacuum to dryness. The crude reaction mixture is chromatographed over a column of 10 times the quantity of silica gel with methylene chloride/5% saturated methanolic ammonia. The first product to be eluted is 6-amino-α-[(4-diphenylmethyl-1-piperazinyl)-methyl]-9H-purine-9-ethanol (foam) (=example 2). The second product to be eluted is 6-amino-α-[(4-diphenylmethyl-1-piperazinyl)methyl]-3H-purine-3-ethanol (m.p. from methanol/methylene chloride: 239°-240°) (=Example 1). The third product obtained is 6-amino-α-[(4-diphenyl-methyl-1-piperazinyl)methyl]-7H-purine-7-ethanol (m.p. 220°-222° [from methano]) (=example 3).

The epoxide used as the starting product is obtained as follows:

100 g of 1-diphenylmethylpiperazine and 250 ml of epichlorohydrin are dissolved in 250 ml of methylene chloride, and then 26 g of tetrabutylammonium bromide in 120 ml of 50% caustic soda are added. The reaction mixture (2 phases) is stirred for 15 hours at room temperature. Then; the methylene chloride is removed in a vacuum, ether is added to the reaction mixture, and the organic phase is extracted several times with water. 1-diphenyl-methyl-4-(2,3-epoxypropyl)-piperazine (m.p. 101°-102°) is obtained from the organic phase.

The following compounds of formula I are obtained analogously to Example 1 (if not otherwise stated, by reacting the corresponding compounds of formula II with corresponding compounds of formula III, in which $R_x$ denotes

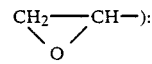

| Example no. | $R_1$ | $R_2$ | $R_3$ | R | position of side chain on the purine ring | configuration* | m.p. and possible optical rotation |
|---|---|---|---|---|---|---|---|
| 4[2] | —NHCH$_3$ | H | H | Diphenylmethyl | 9 | rac. | b 97–98° |
| 5[2] | —NHCH$_3$ | H | H | Diphenylmethyl | 3 | rac. | b 196–197° |
| 6[3] | —N(C$_2$H$_5$)$_2$ | H | H | Diphenylmethyl | 9 | rac. | b foam |
| 7[3] | —N(C$_2$H$_5$)$_2$ | H | H | Diphenylemthyl | 3 | rac. | b foam |
| 8[4] | —N⬡ | H | H | Diphenylmethyl | 9 | rac. | b foam |
| 9[4] | —N⬡ | H | H | Diphenylemthyl | 3 | rac. | b 141–142° |
| 10[5] | —OH | H | H | Diphenylmethyl | 9 | rac. | b 196–197° |
| 11[1] | —OCH$_3$ | H | H | Diphenylmethyl | 9 | rac. | b 134–136° |
| 12[1] | —OCH$_3$ | H | H | Diphenylmethyl | 7 | rac. | b 114–115° |
| 13[6] | —NHCOCH$_3$ | H | H | Diphenylmethyl | 9 | rac. | b 135–136° |
| 14[7] | —NH$_2$ | H | H | Diphenylmethyl | 9 | (R) | tch 228–230° $[α]_D^{20}$ = +7° (c = 1 in H$_2$O) |
| 15[8] | —NH$_2$ | H | H | Diphenylmethyl | 9 | (S) | tch 220° $[α]_D^{20}$ = −6,8° (c = 1 in H$_2$O) |

-continued

| Example no. | $R_1$ | $R_2$ | $R_3$ | R | position of side chain on the purine ring | configuration* | m.p. and possible optical rotation |
|---|---|---|---|---|---|---|---|
| 16[6] | —NHCO—C₆H₅ | H | H | Diphenylmethyl | 9 | rac. | b 198–199° |
| 17 | —NH₂ | H | H | Diphenylmethyl | 7 | (S) | b 150–151°<br>$[\alpha]_D^{20} = +30,8°$<br>(c = 1 in Methanol) |
| 18 | —NH₂ | H | H | Diphenylmethyl | 3 | (S) | zfu 181–185°<br>$[\alpha]_D^{20} = +26,6°$<br>(c = 0,5 in Methanol) |
| 19 | —NH₂ | H | H | Diphenylmethyl | 3 | (R) | zfu 185°<br>$[\alpha]_D^{20} = -27,6°$<br>(c = 0,5 in Methanol) |
| 20[2] | —NHCH₃ | H | H | Diphenylmethyl | 9 | (S) | bmo 127–128°<br>$[\alpha]_D^{20} = -2,9°$<br>(c = 2 in Methanol) |
| 21[2] | —NHCH₃ | H | H | Diphenylmethyl | 9 | (R) | zfu 175–177°<br>$[\alpha]_D^{20} = +1,4°$<br>(c = 0,5 in Methanol) |
| 22 | —NH₂ | H | H | —(CH₂)₃—CH(φ-F(p))(φ-F(p)) | 9 | rac. | zfu 180–183° |
| 23[9] | —NH—CH(CH₃)₂ | H | H | Diphenylmethyl | 9 | rac. | b 137–138° |
| 24[9] | —NH—CH(CH₃)₂ | H | H | Diphenylmethyl | 3 | rac. | b 193–195° |
| 25[1] | —OCH₃ | H | H | Diphenylmethyl | 9 | (S) | b 153–154°<br>$[\alpha]_D^{20} = -8,9°$<br>(c = 1 in Methanol) |
| 26[1] | —OCH₃ | H | H | Diphenylmethyl | 7 | (S) | b 166–167°<br>$[\alpha]_D^{20} = -5,4°$<br>(c = 1 in Methanol) |
| 27[10] | —NHC₂H₅ | H | H | Diphenylmethyl | 9 | rac. | b foam |
| 28[10] | —NHC₂H₅ | H | H | Diphenylmethyl | 3 | rac. | b 162–164° |
| 29 | H | H | H | Diphenylmethyl | 9 | rac. | zml 142–144° |
| 30 | H | H | H | Diphenylmethyl | 7 | rac. | b 145–147° |
| 31 | Cl | H | H | Diphenylmethyl | 9 | rac. | dch 217–220° |
| 32 | Cl | H | H | Diphenylmethyl | 7 | rac. | b foam |
| 33[11] | —NH₂ | H | CF₃ | Diphenylmethyl | 9 | rac. | b 157–158° |
| 34[12] | —NH₂ | H | CH₃ | Diphenylmethyl | 9 | rac. | zfu 189–191° |
| 35 | —NH₂ | H | NH₂ | Diphenylmethyl | 9 | rac. | b 141–142° |
| 36 | —NH₂ | H | Cl | Diphenylmethyl | 3 | rac. | b 155–157° |
| 37 | —NH₂ | H | Br | Diphenylmethyl | 3 | rac. | b 185–186° |

-continued

| Example no. | R₁ | R₂ | R₃ | R | position of side chain on the purine ring | configuration* | m.p. and possible optical rotation |
|---|---|---|---|---|---|---|---|
| 38[13] | —NHCOCH₃ | NHCOCH₃ | H | Diphenylmethyl | 9 | rac. | b 225–227° |

* = on the carbon atom of the side chain which bears the hydroxy
rac. = racemic
b = in free form as a base
tch = in salt form as a trihydrochloride
zfu = bis-hydrogenfumarate
bmo = bis-malonate
zml = bis-hydrogenmaleinate
dch = di-hydrochloride

[1] The 6-methoxypurine (m.p. 198°) used as the starting product is obtained by reacting 6-chloropurine with sodium methylate in methanol
[2] The 6-methylaminopurine (m.p. 300°, decomp.) used as the starting product is obtained by reacting 6-chloropurine with methylamine
[3] The 6-diethylaminopurine (m.p. 210–212°) used as the starting product is obtained by reacting 6-chloropurine with diethylamine
[4] The 6-piperidinopurine (m.p. 232–234°) used as the starting product is obtained by reacting 6-chloropurine with piperidine
[5] By reacting the compound of example 2 with sodium nitrite in diluted sulphuric acid at 70°
[6] By means of acetylation of the compound of example 2
[7] The adenine is reacted with R-2,2-dimethyl-4-tosyloxymethyl-1,3-dioxolane, then the isopropylidene protecting group is split off with acetic acid. the product (m.p. 202°; $[\alpha]D^{20} = -45.7°$ in H₂O) is tosylated and the tosylate obtained (m.p. 150°, indefinite) is reacted with 1-diphenylmethylpiperazine
[8] The adenine is reacted with S-benzyloxymethylethylene oxide ($[\alpha]D^{20} = -9.6°$), then the benzyl protecting group is split off by means of hydrogenation in presence of palladium on charcoal, the diol obtained (m.p. 203–204°; $[\alpha]D^{20} = +45.8°$ in H₂O) is tosylated and the toslyate obtained (m.p. 150°. indefinite) is reacted with 1-diphenylmethylpiperazine.
[9] The 6-isopropylaminopurine (m.p. 193–194°) used as the starting product is obtained by reacting 6-chloropurine with isopropylamine
[10] The 6-ethylaminopurine (m.p. 221–223°) used as the starting product is obtained by reacting 6-chloropurine with ethylamine
[11] The 8-trifluoromethyladenine (m.p. >300°) used as the starting product is obtained by reacting 4,5,6-triaminopyrimidine with trifluoroacetamide
[12] The 8-methyladenine (m.p. >340°) used as the starting product is obtained by reacting 4,5,6-triaminopyrimidine with acetanhydride
[13] The 2,6-bis-acetaminopurine (m.p. 280–285°) used as the starting product is obtained by reacting 2,6-diaminopurine with acetanhydride The (S)-1-diphenylmethyl-4-(2,3-epoxypropyl)piperazine used as starting product in examples 17, 18, 20, 25 and 26 is prepared as follows:

1-diphenylmethylpiperazine is heated together with an equimolar amount of R-glyzerineglycide in isopropanol during 2 hours to 50°. The formed (S)-1-diphenyl-methyl-4-(2,3-dihydroxypropyl)piperazine is reacted at −10° to −20° with p-toluenesulfochloride in methylenechloride in the presence of triethylamine, then a methanolic sodiummethylat solution is added.

The above reaction product crystallises from ether/hexane in the form of white needles, m.p.=84° to 85°, $[\alpha]D^{20} = -14,6°$ (c=2 in methanol).

The compounds according to the invention in free form or in the form of their physiologically acceptable salts are notable for their interesting pharmacodynamic properties. They can be used as medicaments.

This can be shown in standard tests.

The compounds according to the invention have cardiotonic properties. On the rat which has been anaesthetised with Inactin(R) at a dosage of about 0.03 mg/kg to 3 mg/kg i.v., they effect an increase in the contractile force of the left ventricle. When using the compound of example 20, the increase is 12% and 61% at dosages of 0.1 and 1.0 mg/kg i.v. The corresponding values for amrinone are 7% and 29%.

On the isolated, acutely insufficient rabbit's heart, increases in conctractile force could be established at dosages of about 0.1 μg/min to 100 μg/min. For the compound of example 20, increases of 7% and 47% are established at dosages of 10 and 100 μg/min. With amrinone, the increase in contractile force is 3% at 100 μg/min and 15% at 2000 μg/min.

This test is effected as follows:

The test is concerned with a method by LANGENDORFF (1895) in which the apparatus is modified, but the principle is unchanged. Male rabbits (2.2 to 2.5 kg) are given 5 mg/kg heparin by an i.v. injection, and are killed 10 minutes later by a blow to the neck, and drained of blood by opening the carotid artery. After opening the chest cavity, a cannula is connected to the aorta and is perfused with oxygenated (95% O₂ and 5% CO₂) Tyrode's solution of 37° C. The Tyrode's solution has the following composition (g/liter): NaCl 8 g; KCl 0.2 g; CaCl₂ 0.2 g; MgCl₂ 0.1 g; NaHCO₃ 1 g; NaH₂PO₄ 0.05 g; glucose 1 g. After the heart has been exposed, it is suspended from the perfusion apparatus. The heart is perfused at a constant pressure of 60 cm H₂O (44 mm Hg). A strain-gauge is fixed into the left ventricular wall without putting too much strain on the coronary vessels. The active electrodes for electric stimulation are placed in the right atrium and connected to a Grass-Stimulator Type S5. The left-ventricular contractile force, measured isometrically in grams with a strain-gauge, is recorded on a Schwarzer stenographer. In order to raise the sensitivity of the heart, the organs are damaged with high concentrations of isoprenaline. 10 minute infusions of 0.5 or 1 μg/min isoprenaline repeated two to three times, lead, subsequently, to a reduction in contractile force. A criterion for an acutely insufficient heart is a reduction in contractile force of ca. 40%. The test substance is respectively infused for 10 minutes.

Because of this activity, the compounds according to the invention can be used as cardiotonics, e.g. in the therapy of cardiac insufficiency.

For the above-mentioned use as cardiotonics, the dosage to be used varies according to the substance used, the type of administration and the desired treatment. In general however, satisfactory results are obtained with a daily dosage of approximately 0.01 to 10 mg per kg body weight; if necessary, administration may take place in 2 to 4 parts or even in sustained release form. For larger mammals, the daily dosage is in the region of approximately 1 to 500 mg; suitable dosage forms for e.g. oral or non-oral administration generally contain about 0.25 to 250 mg, together with solid or liquid carrier substances.

In addition, the compounds according to the invention possess anti-arrhythmic properties. They effect a prolonging of the functional refractory period in the left guniea-pig atrium at bath concentrations of about $10^{-7}$M to $10^{-4}$M (R. Hof and G. Scholtysik, J. Cardiovasc. Pharm. 5 [1983] 176–183).

They can therefore be used as anti-arrhythmics, e.g. in the treatment of cardiac irregularities, such as supraventricular tachycardia or fibrillation.

For the above-mentioned use as anti-arrhythmics, the dosage to be used varies according to the substance used, the type of administration and the desired treatment. In general however, satisfactory results are obtained with a daily dosage of approximately 0.01 to 10 mg per kg body weight; if necessary, administration may take place in 2 to 4 parts or even in sustained release form. For larger mammals, the daily dosage is in the region of approximately 0.1 to 500 mg; suitable dosage forms for e.g. oral or non-oral administration generally contain about 0.025 to 250 mg, together with solid or liquid carrier substances.

The compound of Example 20 is preferred.

The compounds according to the invention in free form or in the form of their physiologically acceptable salts may be administered alone or in a suitable dosage form. The medicinal forms, e.g. solution or a tablet, may be produced analogously to known methods.

The invention thus relates also to medicaments which contain the compounds according to the invention in free form or in the form of their physiologically acceptable salts, as well as the use of the compound according to the invention for the production of these medicaments that are useful in the treatment of cardiac insufficiency and cardiac irregularity. The conventional pharmaceutical adjuvants and carriers may be used in their production.

I claim:

1. The compounds of formula I,

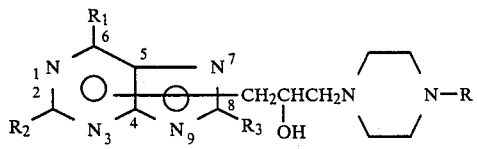

wherein
R signifies diphenylalkyl with 13 to 17 carbon atoms or diphenylalkyl with 13 to 17 carbon atoms which is monosubstituted or disubstituted by the same or different substituents in one or both phenyl rings by alkyl with 1 to 4 carbon atoms, alkoxy with 1 to 4 carbon atoms and/or halogen with an atomic number of 9 to 35, $R_1$ denotes hydrogen, halogen with an atomic number of 9 to 35, $R_1$ denotes hydrogen, halogen with an atomic number of 9 to 35, amino, alkylamino with 1 to 4 carbon atoms, dialkylamino with independently 1 to 4 carbon atoms in the alkyl radicals, 1-piperidino, alkanoylamino with a total of 2 to 5 carbon atoms, hydroxy, alkoxy with 1 to 4 carbon atoms, sulphhydryl, alkylthio with 1 to 4 carbon atoms, benzoylamino or pyridinylcarbonylamino, $R_2$ signifies hydrogen, hydroxy, amino or alkanoylamino with a total of 2 to 5 carbon atoms and $R_3$ signifies hydrogen, alkyl with 1 to 4 carbon atoms, trifluoromethyl, amino or halogen with an atomic number of 9 to 35, in free form or in salt form.

2. The compounds defined in claim 1 in optically active form with respect to the carbon atom of the side chain which bears the hydroxy group.

3. A compound selected from 6-amino-α-[(4-diphenylmethyl-1-piperazinyl)methyl]-3H-purine-3-ethanol 6-amino-α-[(4-diphenylmethyl-1-piperazinyl)methyl]-9H-purine-9-ethanol
6-amino-α-[(4-diphenylmethyl-1-piperazinyl)methyl]-7H-purine-7-ethanol
6-methylamino-α-[(4-diphenylmethyl-1-piperazinyl)methyl]-9H-purine-9-ethanol
6-methylamino-α-[(4-diphenylmethyl-1-piperazinyl)methyl]-3H-purine-3-ethanol
6-diethylamino-α-[(4-diphenylmethyl-1-piperazinyl)methyl]-9H-purine-9-ethanol
6-diethylamino-α-[(4-diphenylmethyl-1-piperazinyl)methyl]-3H-purine-3-ethanol
6-piperidino-α-[(4-diphenylmethyl-1-piperazinyl)methyl]-9H-purine-9-ethanol
6-piperidino-α-[(4-diphenylmethyl-1-piperazinyl)methyl]-3H-purine-3-ethanol
6-hydroxy-α-[(4-diphenylmethyl-1-piperazinyl)methyl]-9H-purine-9-ethanol
6-methoxy-α-[(4-diphenylmethyl-1-piperazinyl)methyl]-9H-purine-9-ethanol
6-methoxy-α-[(4-diphenylmethyl-1-piperazinyl)methyl]-7H-purine-7-ethanol
6-acetylamino-α-[(4-diphenylmethyl-1-piperazinyl)methyl]-9H-purine-9-ethanol
(+)-(R)-6-amino-α-[(4-diphenylmethyl-1-piperazinyl)methyl]-9H-purine-9-ethanol
(−)-(S)-6-amino-α-[(4-diphenylmethyl-1-piperazinyl)methyl]-9H-purine-9-ethanol
6-benzoylamino-α-[(4-diphenylmethyl-1-piperazinyl)methyl]-9H-purine-9-ethanol
(+)-(S)-6-amino-α-[(4-diphenylmethyl-1-piperazinyl)methyl]-7H-purine-7-ethanol
(+)-(S)-6-amino-α-[(4-diphenylmethyl-1-piperazinyl)methyl]-3H-purine-3-ethanol
(−)-(R)-6-amino-α-[(4-diphenylmethyl-1-piperazinyl)methyl]-3H-purine-3-ethanol
(−)-(S)-6-methylamino-α-[(4-diphenylmethyl-1-piperazinyl)methyl]9H-purine-9-ethanol
(+)-(R)-6-methylamino-α-[(4-diphenylmethyl-1-piperazinyl)methyl]9H-purine-9-ethanol
6-amino-α-[(4-di-p-fluorophenyl-1-but-4-yl-1-piperazinyl)methyl]9H-purine-9-ethanol
6-isopropylamino-α-[(4-diphenylmethyl-1-piperazinyl)methyl]-9H-purine-9-ethanol
6-isopropylamino-α-[(4-diphenylmethyl-1-piperazinyl)methyl]-3H-purine-3-ethanol
(−)-(S)-6-methoxy-α-[(4-diphenylmethyl-1-piperazinyl)methyl]-9H-purine-9-ethanol
(−)-(S)-6-methoxy-α-[(4-diphenylmethyl-1-piperazinyl)methyl]-7H-purine-7-ethanol
6-ethylamino-α-[(4-diphenylmethyl-1-piperazinyl)methyl]-9H-purine-9-ethanol
6-ethylamino-α-[(4-diphenylmethyl-1-piperazinyl)methyl]-3H-purine-3-ethanol
α-[(4-diphenylmethyl-1-piperazinyl)methyl]-9H-purine-9-ethanol
α-[(4-diphenylmethyl-1-piperazinyl)methyl]-7H-purine-7-ethanol
6-chloro-α-[(4-diphenylmethyl-1-piperazinyl)methyl]-9H-purine-9-ethanol
6-chloro-α-[(4-diphenylmethyl-1-piperazinyl)methyl]-7H-purine-7-ethanol
6-amino-8-trifluormethyl-α-[(4-diphenylmethyl-1-piperazinyl)methyl]-9H-purine-9-ethanol
6-amino-8-methyl-α-[(4-diphenylmethyl-1-piperazinyl)methyl]-9H-purine-9-ethanol
6,8-di-amino-α-[(4-diphenylmethyl-1-piperazinyl)methyl]-9H-purine-9-ethanol 6-amino-8-chloro-α-[(4-diphenylmethyl-1-piperazinyl)methyl]-3H-purine-3-ethanol 6-amino-8-bromo-α-[(4-diphenylmethyl-1-piperazinyl)methyl]-3H-purine-3-ethanol 2,6-di-acetylamino-α-[(4-diphenylmethyl-1-piperazinyl)methyl]-9H-purine-9-ethanol each in free form or in salt form.

4. Medicaments, characterised in that they contain the compounds defined in claim 1 in free form or in the form of their physiologically acceptable salts.

5. A method of treating cardiac insufficiency and cardiac irregularity which comprises administering to a subject in need of such a treatment a therapeutically effective amount of a compound of claim 1 in free form or in physiologically acceptable salt form.

6. A compound according to claim 1, in which the substituent

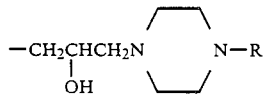

where R is as defined in claim 1, is bonded in the 3, 7 or 9 positions.

7. A compound according to claim 6, in which the substituent is bonded in the 3 or 9 position.

8. A compound according to claim 1, in which the alkylene part of the diphenylalkyl contains 1, 3 or 4 carbon atoms.

9. A compound according to claim 1, in which the alkylene part of the diphenylalkyl contains 1 or 4 carbon atoms.

10. A compound according to claim 1, is which R is diphenylmethyl.

11. A pharmaceutical composition useful in treating cardiac insufficiency and cardiac irregularity comprising a therapeutically effective amount of a compound of claim 1 and a pharmaceutically acceptable carrier therefore.

* * * * *